(12) United States Patent
Kwon et al.

(10) Patent No.: US 8,624,032 B2
(45) Date of Patent: Jan. 7, 2014

(54) COMPOUND LIBRARIES MADE THROUGH PHOSPHINE-CATALYZED ANNULATION/TEBBE/DIELS-ALDER REACTIONS

(71) Applicants: The Regents of the University of California, Oakland, CA (US); The University of Connecticut, Farmington, CT (US)

(72) Inventors: Ohyun Kwon, Los Angeles, CA (US); Gabriel Fenteany, Storrs, CT (US)

(73) Assignees: The Regents of the University of California, Oakland, CA (US); The University of Connecticut, Farmington, CT (US)

( * ) Notice: Subject to any disclaimer, the term of this patent is extended or adjusted under 35 U.S.C. 154(b) by 0 days.

(21) Appl. No.: 13/673,719

(22) Filed: Nov. 9, 2012

(65) Prior Publication Data
US 2013/0143916 A1 Jun. 6, 2013

Related U.S. Application Data

(60) Provisional application No. 61/557,850, filed on Nov. 9, 2011.

(51) Int. Cl.
*C07D 217/22* (2006.01)
*C07D 221/02* (2006.01)
*C07D 217/00* (2006.01)
*C07D 295/00* (2006.01)
*C07D 401/00* (2006.01)

(52) U.S. Cl.
USPC ........... 546/141; 546/142; 546/196; 546/112; 546/139; 546/184

(58) Field of Classification Search
USPC ........................................... 546/139
See application file for complete search history.

(56) References Cited

PUBLICATIONS

Wang, et al. "Diversity Through a Branched Reaction Pathway: Generation of Multicyclic Scaffolds and Identification of Antimigratory Agents," Chemistry, A European Journal, Nov. 9, 2010, vol. 17, Issue 2, pp. 649-654, with supplemental material.

*Primary Examiner* — John Mabry
*Assistant Examiner* — Daniel Carcanague
(74) *Attorney, Agent, or Firm* — John P. O'Banion

(57) ABSTRACT

A method for producing libraries of structurally and stereochemically diverse molecules that can be screened for biological or chemical activity. A library of 91 heterocyclic compounds composed of 16 distinct scaffolds was synthesized through a sequence of phosphine-catalyzed ring-forming reactions, Tebbe reactions, Diels-Alder reactions, and, in some cases, hydrolysis to illustrate the methods. Three compounds inhibiting migration of human breast cancer cells are identified from the library.

1 Claim, 7 Drawing Sheets

US 8,624,032 B2

COMPOUND LIBRARIES MADE THROUGH PHOSPHINE-CATALYZED ANNULATION/TEBBE/DIELS-ALDER REACTIONS

STATEMENT REGARDING FEDERALLY SPONSORED RESEARCH OR DEVELOPMENT

This invention was made with Government support under Grant Numbers GM071779, GM081282, and GM077622, awarded by the National Institutes of Health. The Government has certain rights in this invention.

CROSS-REFERENCE TO RELATED APPLICATIONS

This application is a nonprovisional of U.S. provisional patent application Ser. No. 61/557,850 filed on Nov. 9, 2011, incorporated herein by reference in its entirety.

INCORPORATION-BY-REFERENCE OF MATERIAL SUBMITTED ON A COMPACT DISC

Not Applicable

BACKGROUND OF THE INVENTION

1. Field of the Invention

This invention pertains generally to synthesis schemes and methods for producing small organic molecules, and more particularly to compositions and methods for producing libraries of structurally and stereochemically diverse heterocyclic compounds with distinct scaffolds and functional molecules that can be screened for biological or chemical activity. Several molecules that were shown to inhibit human breast cancer cell migration were identified from one functional analysis of the library.

2. Description of Related Art

The relationship between the structure and function of interacting molecules is a fundamental issue in the study of biological and other chemistry-based systems. For example, structure-function relationships are important in understanding the function of enzymes, cellular communication, cellular control and feedback mechanisms, and the biological activity of pharmaceutical agents.

Certain macromolecules are known to interact and bind to other molecules that have a specific 3-dimensional spatial and electronic distribution resulting in predictable biological or chemical activity. The identification of structures and molecular interactions are important in the development of pharmacological or therapeutic agents that are useful in human or animal health care, agriculturally useful chemicals, selective biocides for insects, weeds, or other pests, as well as catalytic and other entities useful in a variety of industrial processes.

Drug discovery has evolved from essentially random screening of natural products into a scientific process that not only includes the rational and combinatorial design of large numbers of synthetic molecules as potential bioactive or chemical agents but also includes the mechanistic and structural characterization of their biological targets.

However, there are significant hurdles to overcome in order to predict a desired function based on structure alone as well as in the identification and design of high affinity ligands for a particular biological target of interest. These hurdles include the difficulty in defining rules for predicting whether a particular small molecule will interact with proteins along with the task of elucidating the structure of ligands and targets and the nature of their interactions.

Another hurdle is the large number of compounds that need to be generated in order to identify and evaluate new leads or to optimize existing leads. The structural similarities and dissimilarities between these large numbers of compounds need to be identified and the structural features need to be correlated with the activity and binding affinity, because small structural changes can lead to large effects on the overall biological activities of compounds.

One approach toward broadening the understanding of the relationship between structure and function is to generate many new small molecules that potentially modulate the functions of a particular protein and to study the interactions between them. In this context, collections of compound libraries can be established as common starting points for the study of chemical genetics and the discovery of new drugs. The strategy of small compound discovery has moved from the selection of drug leads from among compounds that are individually synthesized and tested to the creation and screening of large collections of compounds. These collections may be from natural sources or generated by synthetic methods such as combinatorial chemistry. These collections of compounds may be generated as libraries of individual, well-characterized compounds synthesized, e.g., via high throughput, parallel synthesis or as a mixture or a pool of up to several hundred or even several thousand molecules synthesized by split-mix or other combinatorial methods.

The development of efficient methods for the construction of libraries encompassing the maximum amount of chemical space is a particularly challenging task for organic chemists. Establishing the maximum amount of skeletal diversity is a key factor toward improving the screening efficiency for novel therapeutic leads. Diversity-oriented synthesis (DOS) entails the development of pathways leading to the efficient synthesis of collections of small molecules exhibiting rich skeletal and stereochemical diversity.

Compared with libraries constructed from common scaffolds decorated with diverse substituents, there are very few examples of libraries of small molecules featuring high degrees of skeletal and stereochemical diversity. In addition, although such exercises are undertaken based on the premise that a diverse range of scaffolds should provide a higher chance for discovery of small-molecule biological functional modulators, its actual realization is rarely reported.

The identification of ligands that bind may provide a lead for identifying compounds with a desired biological activity, e.g., as a potential drug candidate. As methods have become available to screen these complex mixtures more effectively, interest in exploiting the "rational design" or the "directed molecular evolution" approaches have increased.

Accordingly, there is a need for a system and method for reliably and efficiently producing libraries of molecules with significant skeletal and stereochemical diversity that can be screened for chemical and biological activity. The present invention satisfies these needs as well as others and is generally an improvement over the art.

BRIEF SUMMARY OF THE INVENTION

The present invention is directed to materials and methods for producing structurally and stereochemically diverse collections or libraries of preferably heterocyclic compounds that can be screened for activity in a variety of applications including screening of therapeutic compound leads. To illustrate the methods, a highly efficient and modular synthesis scheme is used to create a library of 91 multicyclic heterocycles with 16 distinctive scaffolds that was then screened for a specific biological activity. Screening resulted in the identification of three new anti-migratory agents that inhibit the migration and invasion of human breast cancer cells.

The present invention provides a method of producing libraries of heterocyclic compounds with sufficiently high levels of skeletal diversity to explore biologically relevant regions of chemical space. To illustrate the methods, a library of heterocyclic compounds comprising 16 distinct scaffolds was synthesized through a sequence of phosphine-catalyzed ring-forming reactions, Tebbe reactions, Diels-Alder reactions, and, in some cases, hydrolysis.

The diversity-oriented synthesis scheme produced a collection of compounds that exhibited high levels of structural variation both in terms of stereochemistry and the range of scaffolds represented. A simple but powerful sequence of reactions thus led to a highly diverse library of relatively modest size with which to explore biologically relevant regions of chemical space. It is believed that this represents the first report of this sequence of chemical reactions to generate a library of heterocyclic compounds comprising 16 distinct scaffolds.

The small molecules that are produced can be tested in multifarious bio-assays to identify the initial biomodulators. Analogs of the initial hits may then be prepared by expanding upon the described chemistry to generate more potent and selective molecules. From the library that was produced, several molecules were identified that inhibit the migration and invasion of breast cancer cells and may serve as leads for the development of other anti-metastatic agents. The molecules demonstrating anti-migratory activity from the library are diagrammed in FIG. 6, FIG. 7 and FIG. 8.

By way of example, and not of limitation, a preferred method for producing a library of molecules for screening of biological or chemical activity generally comprises the steps of 1) providing or creating an initial set of a variety of molecules that each have at least one ($\alpha,\beta$)-unsaturated ester; 2) methylenate the molecules with a methylenating agent; and 3) performing a Diels-Alder reaction between the methylenated reaction products and electron-deficient molecules to produce a library of compounds.

The ($\alpha,\beta$)-unsaturated ester starting molecules can have a wide variety of structures that can include linear, branched or cyclic substituents. Allenoates are particularly preferred starting materials for the formation of the ($\alpha,\beta$)-unsaturated esters through the phosphine-catalyzed annulation reactions. Ethyl allenoate with alkyl or aryl substituents are one group of preferred starting materials.

In one preferred embodiment of the invention, a library of heterocyclic compounds are created by (a) forming pyrrolines and tetrahydropyridines with at least one ($\alpha,\beta$)-unsaturated ester through phosphine-catalyzed ring formation between allenoates and imines; (b) methylenating the unsaturated esters with Tebbe reagent to produce a variety of ethoxy dienes; and (c) performing a Diels-Alder reaction between the Tebbe reaction products and electron-deficient dienophiles to produce a library of compounds.

The Diels-Alder reaction between the ethoxy dienes and the dienophiles is a further source of skeletal diversity. Preferred dienophiles include N-phenylmaleimide, N-ethylmaleimide, N-benzylmaleimide, secondary aldimines, N-phenyltriazolinedione, tetracyanoethylene, benzoquinone, and 2,6-dichlorobenzoquinone.

According to one aspect of the invention, a system and method for creating libraries of compounds that are structurally and stereochemically diverse that can be screened for biological or chemical activity is provided.

Another aspect of the invention is to provide diversity oriented synthesis methods for producing a variety of heterocyclic compounds.

Another aspect of the invention is to provide a method for the efficient production of collections of small molecules with a diverse range of scaffold structures and substituents.

A further aspect of the invention is to provide molecules that have been shown to have selected biological or chemical activity such as anti-metastatic agents for use in the treatment of disease.

Another object of the invention is to improve the efficiency of the synthesis and screening of novel therapeutic leads.

Still another object of the invention is to provide a method for producing a variety of small molecules for testing in many different types of bio-assays to identify initial biomodulators. Analogs of the initial hits would be prepared by expanding upon the described chemistry for generating more potent and selective molecules.

Another aspect of the invention is to build upon our published work in "Diversity Through a Branched Reaction Pathway: Generation of Multicyclic Scaffolds and Identification of Antimigratory Agents", Chem. Eur. J. 2011, 17, 649-654, and the associated Supporting Information published with the paper. These publications are incorporated herein by reference in their entirety.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWINGS

The invention will be more fully understood by reference to the following drawings which are for illustrative purposes only.

DETAILED DESCRIPTION OF THE INVENTION

Referring more specifically to the drawings, for illustrative purposes one embodiment of the present invention is depicted in the methods and products generally shown in FIG. 1 through FIG. 8. It will be appreciated that the methods may vary as to the specific steps and sequence and the products may vary as to structural details, without departing from the basic concepts as disclosed herein. The steps depicted and/or used in methods herein may be performed in a different order than as depicted in the figures or stated. The steps are merely exemplary of the order these steps may occur. The steps may occur in any order that is desired, such that it still performs the goals of the claimed invention.

The present invention provides methods for producing collections or libraries of structurally and chemically diverse molecules that can be assayed for characteristic biological or chemical activity. The method is an effective tool for chemical and biological studies and the identification of therapeutic lead compounds, macromolecules or macromolecule-ligand complexes.

Figure 1:
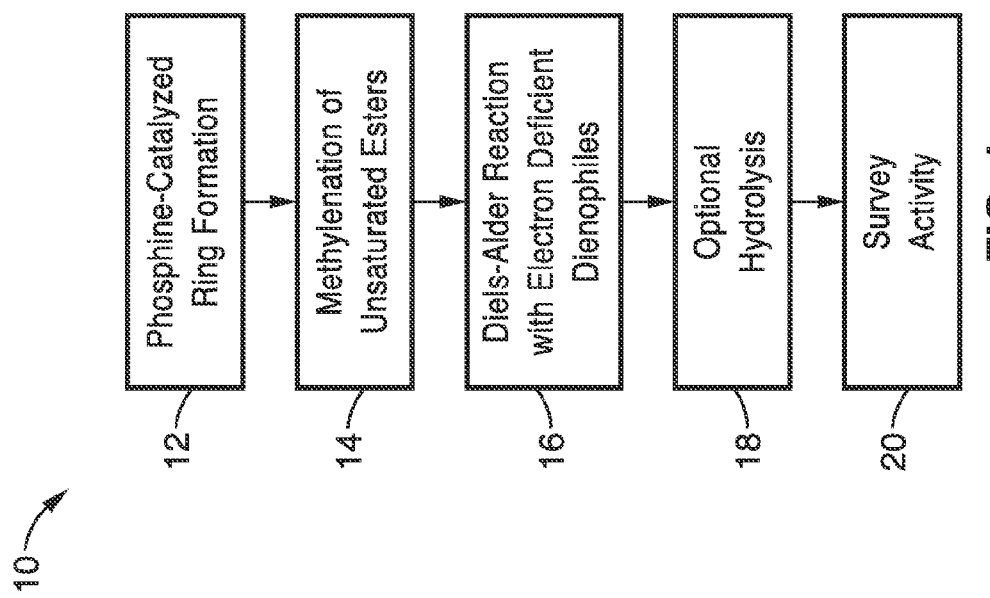
FIG. 1 is a flow diagram of a method of forming a structurally and stereochemically diverse library of heterocyclic compounds according to one embodiment of the invention.

Turning now to FIG. 1, the steps according to a preferred embodiment 10 of the present method for producing a library of compounds using starting materials containing at least one $(\alpha,\beta)$-unsaturated ester group is illustrated. At block 12, various molecules with rings are produced with a phosphine-catalyzed reaction. Cycloaddition of electron-deficient allenes under phosphine catalysis is a robust method for obtaining a variety of carbocycles and heterocycles in an atom-economical manner. The phosphine-catalyzed reactions are typically high yielding and compatible with solid phase synthetic processes.

The pyrrolines and tetrahydropyridines resulting from the phosphine catalysis of allenoates and imines possess a common $(\alpha,\beta)$-unsaturated ester group. While cyclic structures with $(\alpha,\beta)$-unsaturated ester groups are illustrated, it will be understood that many different starting compounds that have unsaturated esters can be used, including linear or branched molecules. For example, a number of reactions transforming aldehydes into $\alpha,\beta$-unsaturated esters have been developed including Wittig reaction variants.

In one embodiment, scaffold diversification was increased through the use of an $\alpha,\beta$ enoate functionality as a handle for highly diastereoselective Michael additions of thiols. Although the conjugate addition of thiols provides only a relatively moderate level of skeletal variation, the pentasubstituted pyrrolidine products are useful starting materials and the versatile chemistry of conjugated enoates might provide a handle for further scaffold diversification.

One group of preferred starting materials for ring formation in the embodiment shown at block 12 of FIG. 1 is allenoates and secondary aldimines. In one embodiment, the allenoates can have alkyl or aryl substituents. In another embodiment, the allenoate substituents include isopropyl, pentyl, butyl or phenyl groups. Ethyl allenoates with alkyl or aryl substituent groups are particularly preferred.

At block 14 of FIG. 1, the starting material or synthesized material provided at block 12 is methylenated. The methylenation of the $\alpha,\beta$-unsaturated ester at block 14 is preferably performed with Tebbe reagent. When the C=O moiety of an $\alpha,\beta$-unsaturated ester is methylenated, the resulting dienol ether (an electron-rich diene) can undergo Diels-Alder reactions at block 16 with electron-deficient dienophiles to generate a variety of fused heterocyclic compounds possessing distinctive frameworks.

Optionally, at block 18, the enol ethers can be hydrolyzed to ketones to increase the diversity of the library.

At block 20 of FIG. 1, the biological or chemical activity of the molecules in the library is assayed. The resulting libraries consist of a complex assortment of molecules that may contain one or more compounds which may associate with a target of interest. The assays at block 20 are designed to identify molecules having a specified chemical activity or bioactivity, as indicated initially by the detection of binding between one or more species in the library and a "target" molecule with which it naturally binds to influence some biological process. Other assays at block 20 may include the isolation of the individual library members and surveying their influence on known chemical reactions, cellular functions or system functions in vivo.

Accordingly, libraries of molecules can be crafted with structurally and stereochemically diverse constituents that can be easily screened for biological or chemical activity.

The invention may be better understood with reference to the accompanying examples, which are intended for purposes of illustration only and should not be construed as in any sense limiting the scope of the present invention as defined in the claims appended hereto.

EXAMPLE 1

Figure 2:
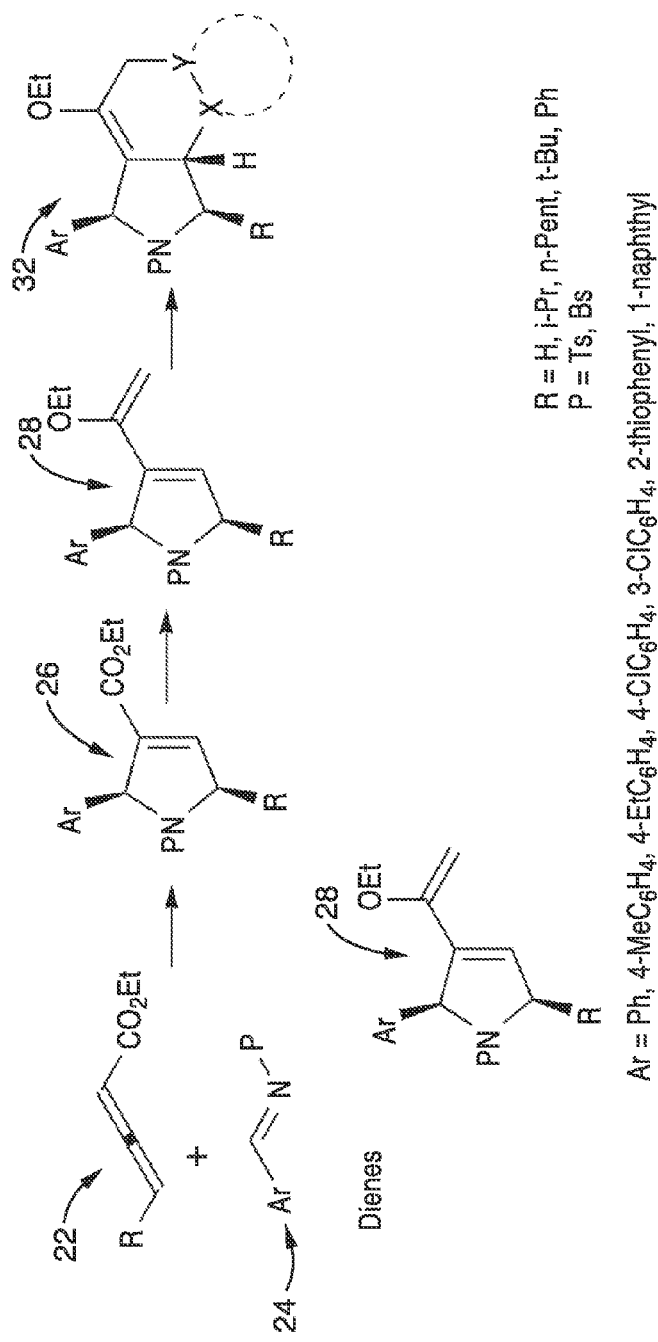
FIG. 2 is a sub-pathway diagram of a method of forming a library according to the embodiment of the invention shown in FIG. 1.
Figure 2:
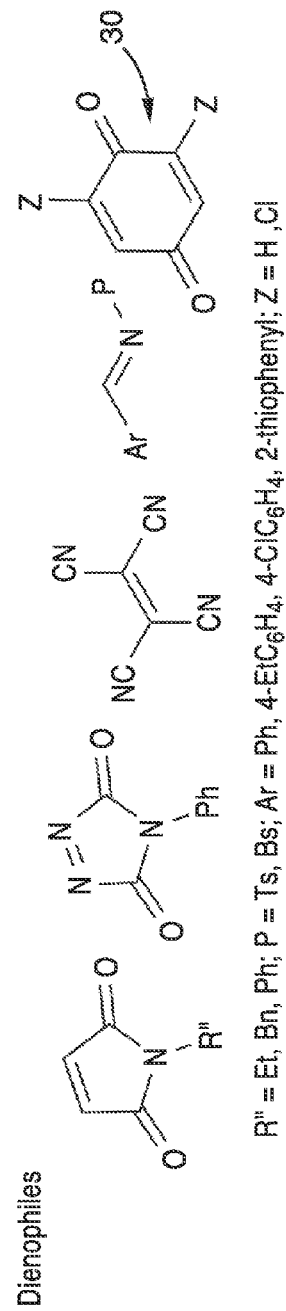

In order to demonstrate the functionality of the library creation methods, a variety of pyrrolines were prepared as starting materials through phosphine-catalyzed ring formation reactions between allenoates and imines in multigram scales. Referring now to FIG. 2, ethyl allenoate 22 was reacted with an imine 24 to produce pyrroline esters 26. As indicated, the allenoates 22 and the imines 24 can have a number of different side groups creating a number of different starting and intermediate step materials. The imine 24 in the pathway illustrated in FIG. 2 is a secondary aldimine where P=benzenesulfonyl (Bs) or tosyl (p-toluenesulfonyl)(Ts) and the Ar=Ph, 4-MeC$_6$H$_4$, 4-EtC$_6$H$_4$, 4-ClC$_6$H$_4$, 3-ClC$_6$H$_4$ 2-thiophenyl or 1-naphthyl groups.

The methylenation of the $\alpha,\beta$-unsaturated esters with the Tebbe reagent produce ethoxy dienes. In this illustration, Tebbe reagent (ca. 1.0 M in toluene, 3.0 eq.) was added dropwise over 10 minutes to a solution of each ester 26 (1.0 mmol) and anhydrous pyridine (0.3 eq.) in dry tetrahydrofuran (THF) (10 mL) at −78° C. (acetone/dry ice). THF was distilled from sodium benzophenone ketyl prior to use. The reddish mixture that was produced was stirred overnight at room temperature, allowing the cooling bath to gradually warm through evaporation of the dry ice. Aqueous NaOH (15%, 0.5 mL) was added dropwise at −78° C. (acetone/dry ice), causing the evolution of CH$_4$. After 1 hour, THF (10 mL) was added to the reaction mixture, which was then stirred for another 4 hours at room temperature. The organic solution was filtered through a Celite pad and the filtrate was concentrated. The crude residue was purified through flash column chromatography (SiO$_2$; 10-25% EtOAc and 1% Et$_3$N in hexanes) to collect the ethoxy diene 28.

As seen in FIG. 2, the various diene 28 structures in the group can have three side substituents structures where R=H, iPr, nPent, tBu or Ph; P=benzenesulfonyl (Bs) or tosyl (p-toluenesulfonyl)(Ts) and Ar=Ph, 4-MeC$_6$H$_4$, 4-EtC$_6$H$_4$, 4-ClC$_6$H$_4$, 3-ClC$_6$H$_4$ 2-thiophenyl and 1-naphthyl. The variety of dienes 28 produced are substrates for Diels-Alder reactions with electron-deficient dienophiles 30 to produce distinctive scaffolds in the library of compounds 32. The Diels-Alder reactions between the Tebbe reaction products (dienes 28) and electron-deficient dienophiles provide another key skeleton-diversifying branch in the pathway.

The twelve dienophile structures 30 that were used are indicated in FIG. 2, where R''=Et, Ph and Bn (benzyl); Ar=Ph, 4-EtC$_6$H$_4$, 4-ClC$_6$H$_4$ and 2-thiophenyl; and Z=H or Cl. Accordingly, maleimide, N-phenyltriazolinedione, tetracyanoethylene, dichlorobenzoquinone and benzoquinone electron-deficient dienophiles 30 were used in Diels-Alder reactions with the various Tebbe reaction products (dienes 28) that were generated in the previous steps.

A solution of 5-15% MeOH in DCM (1.5 mL) was added to a stirred mixture of the diene 28 (0.5 mmol) and the maleimide (4.0 eq.) dienophile under an Argon atmosphere at room temperature. After the reaction had reached completion (16-48 h, TLC), the mixture was concentrated and the crude residue purified through flash column chromatography (SiO$_2$; 30-50% EtOAc in hexanes) to afford the product. A 71% yield of a white solid that decomposed at 180° C. was produced.

A second Dienophile N-phenyltriazolinedione (2.0 eq.) 28 was added to a solution of the diene 28 (0.5 mmol) in DCM (2.0 mL) at 0° C. After the reaction had reached completion (10-60 min, TLC), the mixture was concentrated and the crude residue purified through flash column chromatography (SiO$_2$; 40-60% EtOAc in hexanes) to produce a final product.

Similarly, the diene 28 (0.5 mmol) in DCM (0.5 mL) was added dropwise to a solution of tetracyanoethylene (2.0 eq.) dienophile 30 in DCM (2.0 mL) at 0° C. under an Argon atmosphere. After the reaction had reached completion (30-60 min, TLC), the resulting mixture was concentrated and the crude residue purified through flash column chromatography (SiO$_2$; 25-40% EtOAc in hexanes) to produce the final structures that were added to the library.

Toluene (2.0 mL) was added to a mixture of the diene 28 (0.5 mmol) and 2,6-dichlorobenzoquinone or benzoquinone (4.0 eq.) under an Argon atmosphere. The mixture was then stirred at 80° C. After the reaction had reached completion (2-5 h, TLC), the mixture was concentrated and the crude residue purified through flash column chromatography (SiO$_2$; 25% EtOAc in hexanes) to provide another group of final products.

Another group 32 of compounds for the library was produced with a solution of the diene 28 (0.5 mmol) and dienophile benzoquinone (4.0 eq.) in toluene (2.0 mL) that was stirred at 80° C. under Argon. After the reaction had reached completion (TLC), the mixture was concentrated and the crude product dissolved in a minimal amount of CHCl$_3$. Silica gel (2 g) purged in triethylamine was added and the mixture and stirred at room temperature overnight. After evaporating the solvent, the crude residue was purified through flash column chromatography (SiO$_2$; 20% EtOAc in hexanes) and the final product was collected and made part of the library.

EXAMPLE 2

To further demonstrate the methods and to further diversify the library, tetrahydropyridine rings 38 were synthesized as a starting material with phosphine-catalyzed ring forming reactions between allenoates 34 and imines 36. Referring now to the pathway depicted in FIG. 3, distinctive scaffolds were produced from the tetrahydropyridine starting materials using the same processing steps as described with the pyrrolines in FIG. 2.

Initially, a solution of a tetrahydropyridine ester 38 (1.0 mmol) and anhydrous pyridine (0.3 eq.) was provided and Tebbe reagent (ca. 1.0 M in toluene, 3.0 eq.) was added dropwise over a 10 minute period in dry THF (10 mL) at −78° C. (acetone/dry ice). The produced mixture was stirred overnight at room temperature, allowing the cooling bath to gradually warm through evaporation of the dry ice. Aqueous NaOH (15%, 0.5 mL) was added dropwise at −78° C. (acetone/dry ice), causing the evolution of CH$_4$. After 1 hour, 10 mL of THF was added to the reaction mixture, which was then stirred for another 4 hours at room temperature. The resulting organic solution was filtered through a Celite pad and the filtrate was concentrated. The crude residue was purified through flash column chromatography (SiO$_2$; 10-25% EtOAc and 1% Et$_3$N in hexanes) to produce the dienes 40.

The Tebbe reaction products (dienes 40) were reacted with electron deficient dienophiles 42 through Diels-Alder reactions to produce the final compounds 44 for the library.

As with the pyrrolines in FIG. 2, maleimide, N-phenyltriazolinedione, tetracyanoethylene, dichlorobenzoquinone and benzoquinone electron-deficient dienophiles 42 were used in Diels-Alder reactions with the various Tebbe reaction products (dienes 40) that were generated. The same set of dienophiles 42 was used with diens 40 as were described with dienes 28 in Example 1.

Accordingly, the dienophiles 42 in the set of dienophiles were reacted with the dienes 40. For the maleimide dienophile, a solution of 5-15% MeOH in DCM (1.5 mL) was added to a mixture of the diene 40 (0.5 mmol) and maleimide (4.0 eq.) under an Argon atmosphere and then the mixture was stirred at room temperature. After the reaction had reached completion (16-48 hours, TLC), the mixture was concentrated and the crude residue purified through flash column chromatography (SiO$_2$; 30-50% EtOAc in hexanes) to produce the final product.

A solution of the diene 40, (0.5 mmol) in DCM (0.5 mL) was added dropwise to a solution of N-phenyltriazolinedione (2.0 eq.) dienophile in DCM (2.0 mL) at −78° C. under an Argon atmosphere. After the reaction had reached completion (3-5 hours, TLC), the mixture was concentrated and the crude residue was purified through flash column chromatography (SiO$_2$; 30-50% EtOAc in hexanes) and the final product was collected and added to the library.

A solution of the diene 40, (0.5 mmol) in DCM (0.5 mL) was added dropwise to a solution of tetracyanoethylene (2.0 eq.) dienophile in DCM (2.0 mL) at −78° C. under an Argon atmosphere. After the reaction had reached completion (3-5 hours, TLC), the mixture was concentrated and the dr ratio determined using $^1$H NMR spectroscopy. The crude residue was purified through flash column chromatography (SiO$_2$; 25% EtOAc in hexanes) to produce the final product.

A solution of the diene 40 (0.5 mmol) and benzoquinone (4.0 eq.) dienophile 42 in toluene (2.0 mL) was stirred at 80° C. under an Argon atmosphere. After the reaction had reached completion (5-10 hours, TLC), the mixture was concentrated and the crude residue purified through flash column chromatography (SiO$_2$; 25% EtOAc in hexanes) to produce the final product to be included in the library.

Finally, a solution of the diene 40 (0.5 mmol) and an imine (4.0 eq.) dienophile 42 in toluene (2.0 mL) was stirred at 65° C. under Argon. After the reaction had reached completion (16-24 hours, TLC), the mixture was concentrated and the crude residue purified through flash column chromatography (SiO$_2$; 30-50% EtOAc in hexanes) to provide the final products, which were made part of the library.

EXAMPLE 3

Figure 3:
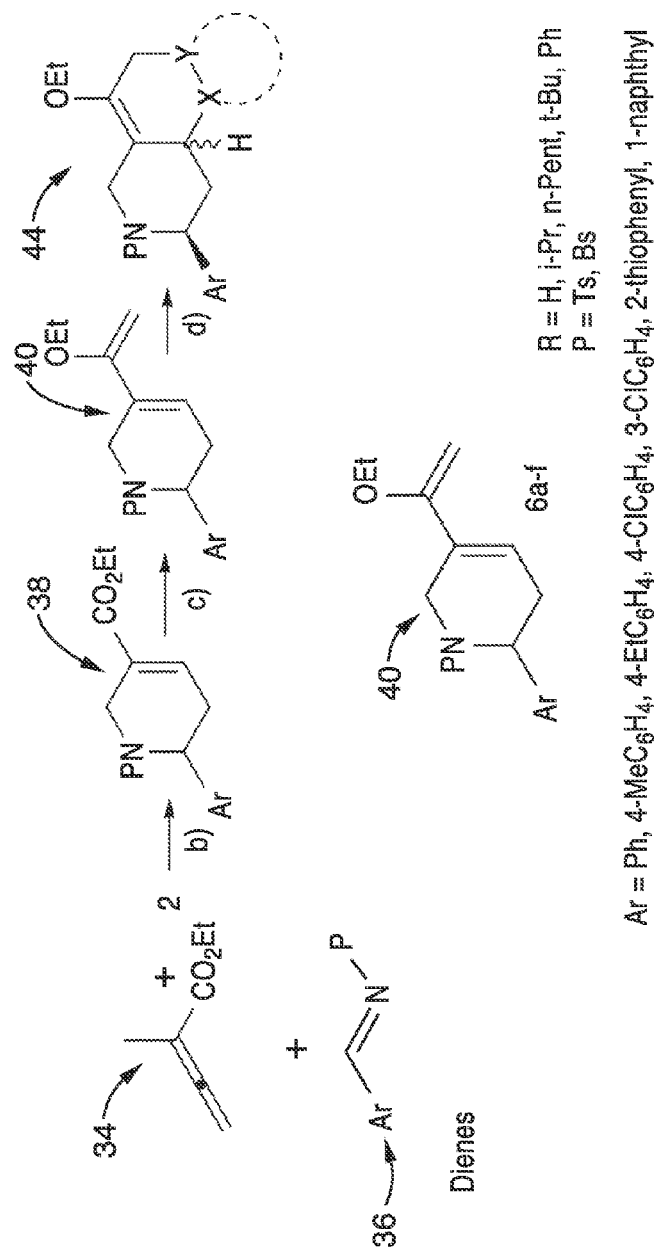
FIG. 3 is a sub-pathway diagram of a method of forming a library according to the embodiment of the invention shown in FIG. 1.
Figure 3:
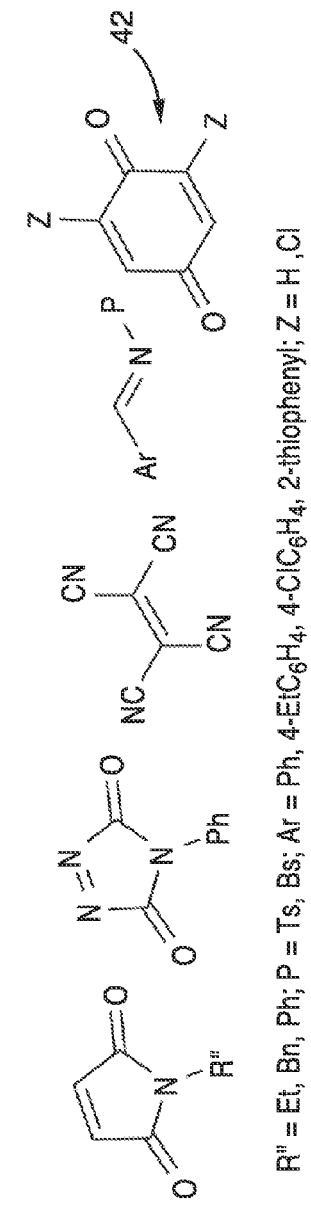
Figure 4A:
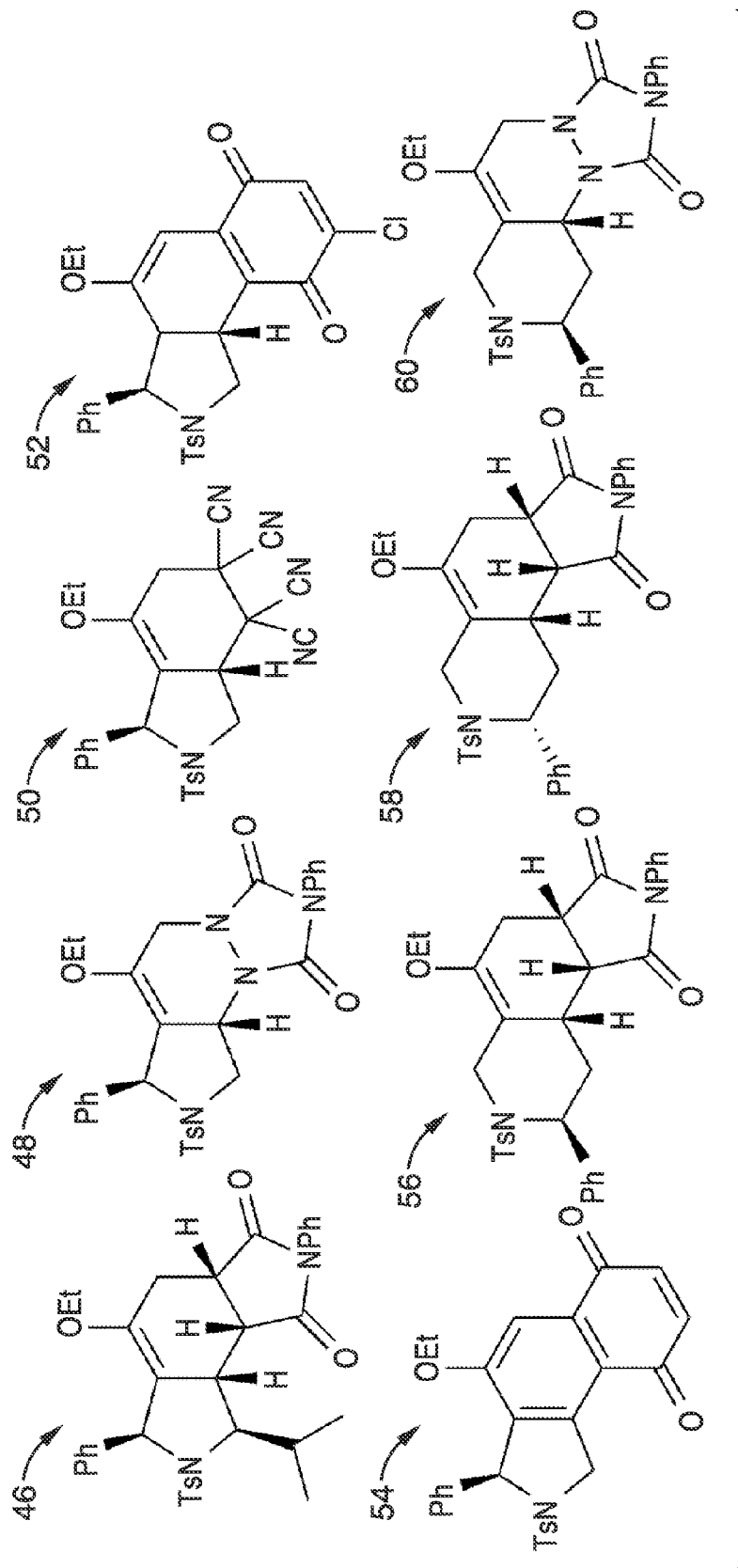
FIG. 4A and FIG. 4B together depict representative compounds possessing the 16 distinctive scaffolds in the library.
Figure 4B:
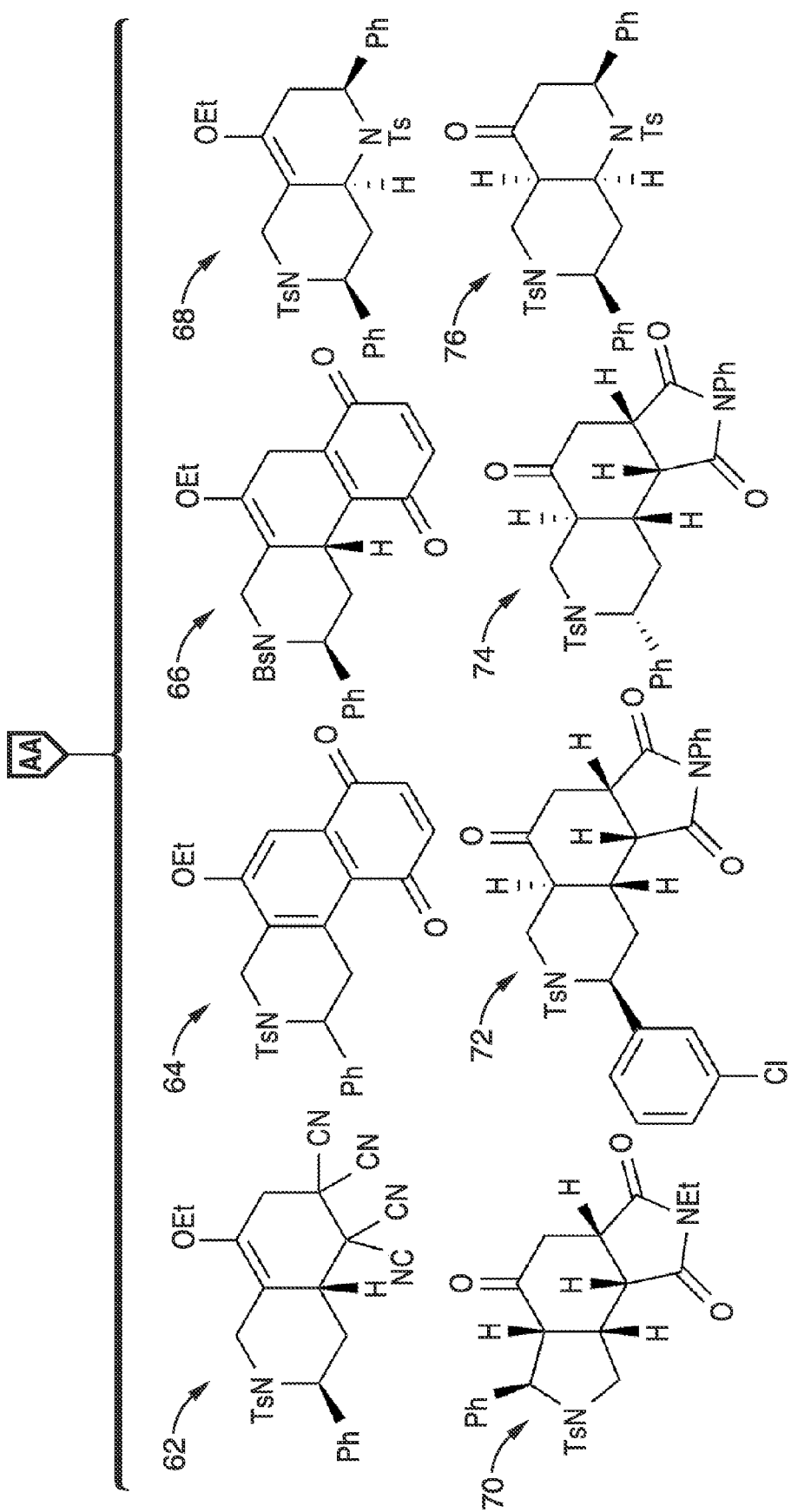

Representative compounds possessing distinctive scaffolds in the assembled library are shown in FIG. 4A and FIG. 4B. These scaffolds were produced from the pathways outlined in FIG. 2 and FIG. 3 as well as in FIG. 5.

Through dienophile screening, maleimides, N-phenyltriazolinedione, tetracyanoethylene, imines, benzoquinone, and 2,6-dichlorobenzoquinone were identified as very good reaction substrates for the Diels-Alder reactions of the prepared ethoxy dienes. Although the reaction yields were only moderate to good (35%-85%), the reaction stereo-selectivities were excellent. Indeed, considering that the compounds in the library possess up to six stereogenic centers, the selectivities of the Diels-Alder reactions are quite remarkable. For example, only single diastereoisomeric products from the cycloadditions of the pyrroline-derived dienes were detected with the diene 28 reaction with maleimides, N-phenyltriazolinedione, tetracyanoethylene, and 2,6-dichlorobenzoquinone and from the cycloadditions of the tetrahydropyridine-derived dienes 40 with N-phenyl triazolinedione, benzoquinone, and imines. The cycloadditions of the dienes 40 of FIG. 3 with the maleimides and tetracyanoethylene dienophiles 42 exhibited diastereoselectivities of up to 6:1 and 10:1, respectively. When benzoquinones were used as the dienophiles 30 or 42, no direct Diels-Alder reaction products were detected. Instead, the oxidized benzoquinones 52 and 66 as well as the naphthoquinones 54 and 64 were detected as illustrated in FIG. 4A and FIG. 4B. Based on the isolation of dienophile-derived hydroquinone byproducts, it is believed that dehydrogenation or dehydrochlorination occurred following the Diels-Alder reactions in the presence of an excess amount of benzoquinone dienophiles. It is also notable that the cyclohexene double bond, resulting from the Diels-Alder reaction, isomerized into conjugation with the benzoquinone 52 as shown in FIG. 4A.

Given the complexity of the structures of the library of compounds, the determination of their structures, especially their stereochemistry, was a challenge. The relative configuration of each scaffold obtained from the Diels-Alder reactions, with the exception of compound 66, was established unequivocally through X-ray crystallographic analysis. The structure of compound 66 was established based on $^1H$, $^{13}C$, DEPT, and COSY NMR spectroscopic and mass spectrometric data. In addition, compound 66, when left at room temperature for over 6 months, was converted into its isomer, which featured its enol ether double bond in conjugation with the benzoquinone motif and is comparable with compound 52 of FIG. 4A. This new isomer compound of compound 66 was then crystallized from the dichloromethane/pentane solution. The X-ray diffraction data of the crystalline solid of the isomer provided the relative configuration of compound 66.

As verified by the X-ray crystallographic analysis, for the dienes 28, the chiral center(s) created in the phosphine-catalyzed [3+2] ring-forming reactions controlled the face from which the dienophile 30 approached the diene 28 in endo-selective Diels-Alder reactions producing scaffolds 46, 48, 50 and 52 of FIG. 4A. In particular, the dienophiles 30 approached the dienes 28 from the face opposite the C2 substituent.

However, the Diels-Alder reactions of the tetrahydropyridine-derived dienes 40 diagrammed in FIG. 3 displayed relatively mixed facial selectivities. For example, the reaction with the maleimide dienophile 42, although endo-selective, produced the two diastereoisomers 56 and 58 of FIG. 4A in a 2:1 ratio, presumably because the C2 stereogenic center was too far removed from the reaction center to exert a significant steric bias.

The dienophiles N-phenyltriazolinedione, tetracyanoethylene, and benzoquinone underwent [4+2] cycloadditions by adding to the diene 40 from the face opposite the C2 aryl group yielding compounds 60, 62 and 66, respectively.

Interestingly, for imine dienophiles, the endo-selective Diels-Alder reaction provided, for example, the octahydro-1,6-naphthyridine compound 68, in which the tosyl group in the tetrahydropyridine ring of the diene 40 controlled the facial approach of the imine dienophile. X-ray crystallography revealed that the tetrahydropyridine 52 and the octahydronaphthyridine 68 featured anti-relationships between their α-phenyl and N-tosyl groups.

EXAMPLE 4

Figure 5:
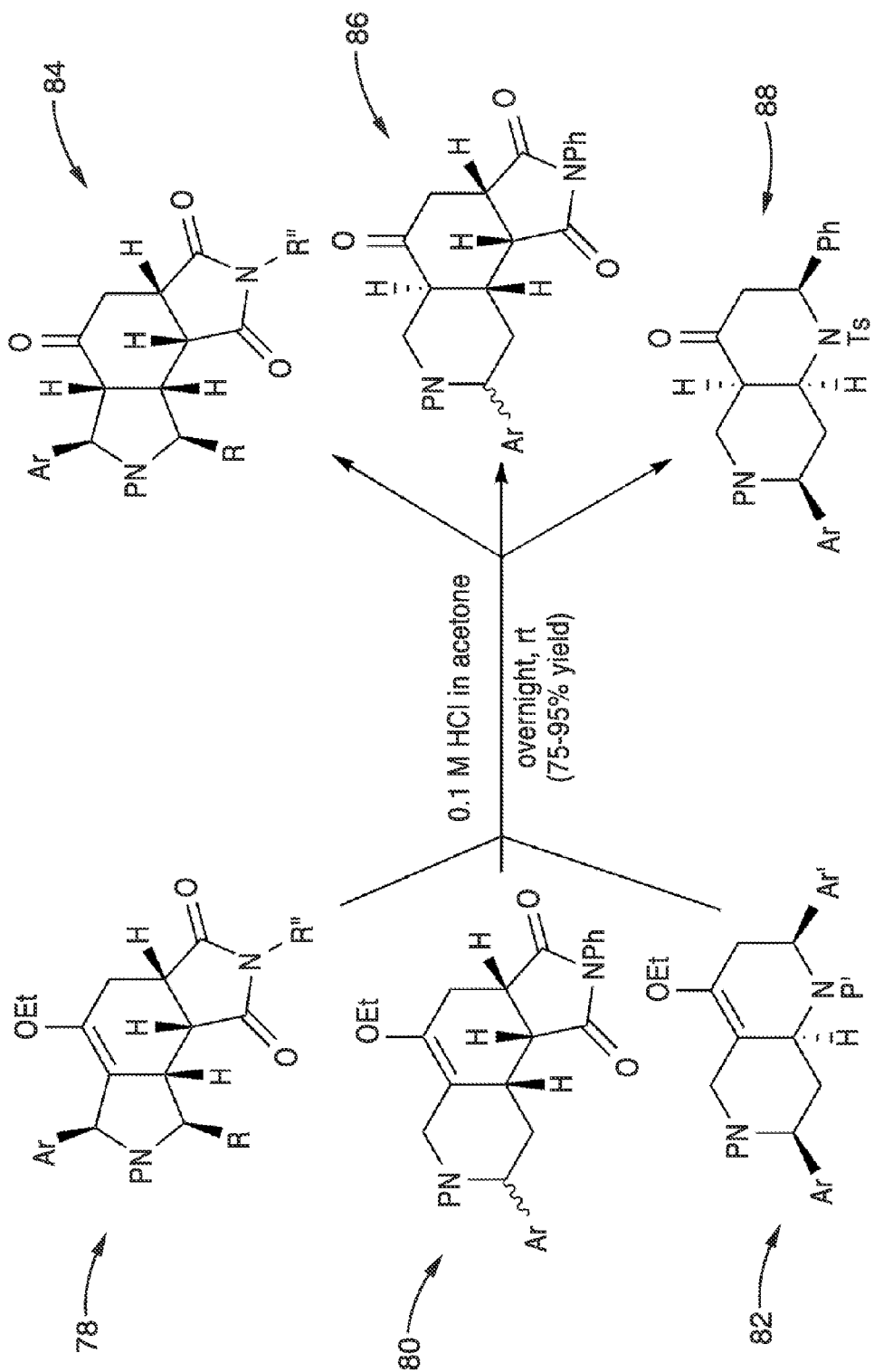
FIG. 5 is a diagram illustrating the optional hydrolysis of enol ethers to ketones step to add further diversity to the library.

The product library diversity was increased with the hydrolysis of enol ethers to ketones as illustrated in FIG. 5 and producing compounds 70, 72, 74 and 76 of FIG. 4B for the library.

The Diels-Alder reaction products featuring enol ether units were also found to be quite stable during purification through silica gel. Most of them could be stored at −20° C. for several months without detectable decomposition. The enol-ethers 78 shown in FIG. 5 can be from the pyrroline group 32 of compounds or enol ethers 80 and 82 from the tetrahydropyridine group 44 of compounds.

The enol ether units 78, 80 and 82 were hydrolyzed to the corresponding ketone products illustrated by compounds 84, 86 and 88 of FIG. 5 upon treatment with a solution of aqueous HCl (0.1 m) in acetone. Concentrated HCl (12.1 M, 0.10 mL) was added dropwise to a solution of the enol ether (78, 80 or 82, 0.17 mmol) in acetone (13 mL). Each mixture was stirred overnight at room temperature. The resulting mixture was concentrated and dissolved in DCM (15 mL). The solution was washed with saturated $NaHCO_3$ (2×10 mL) and brine (2×10 mL) and then dried ($NaSO_4$). The organic phase was concentrated and the crude residue purified through flash column chromatography ($SiO_2$; 30-50% EtOAc in hexanes) to produce the final product. Only a single isomer was detected in each case and the reaction yields ranged from good to excellent (75%-95%).

The ketones that were obtained with this process had cis-5,6-fused rings (compounds 84) or trans-6,6-fused rings (compounds 86). It is also noteworthy that the decahydronaphthyridinones compounds 88 featured a cis-fused [4.4.0] bicyclic framework.

EXAMPLE 5

In order to evaluate the biological activity of the assembled library of 91 compounds, the members of the library were tested for a particular biological activity in an assay for cancer cell migration. Although cell movement is a basic biological phenomenon involved in a range of normal and disease processes, including cancer cell invasion and metastasis, research probes and chemotherapeutics that function through known mechanisms that specifically target cell migration are rare.

Despite the relatively small number of compounds in the library, the broad chemical space covered by the products generated from the branched pathway illustrated in Examples 1-4 greatly increased the chance of identifying compounds exhibiting antimigratory activity. The compound library was first screened in a medium-throughput wound closure assay to identify molecules that inhibited the migration of MDA-MB-231 human breast cancer cells. It was found that compound 90 shown in FIG. 6, compound 92 shown in FIG. 7 and compound 94 shown in FIG. 8 exhibited subtoxic antimigratory activity in the wound closure assay (See Table 1).

In the wound closure assay, MDA-MB-231 cells (American Type Culture Collection number: HTB-26) were cultured in 75 $cm^2$ tissue culture flasks with growth medium (DMEM containing 10% fetal bovine serum) at 37° C. under 5% $CO_2$ in a humidified tissue culture incubator. The cells were grown to 80% confluence and then treated with trypsin, collected, and replated in 96-well tissue culture plates for initial screening. Once confluent, the cell cultures were treated with compounds at various concentrations or with DMSO carrier solvent alone with fresh growth medium. In all cases, the final DMSO concentration was 0.05%. After 30 minutes, the cell cultures were wounded with a sterile micropipette tip, and the wound closure experiments were performed essentially as described previously.

Compounds were first screened at 50 μm and evaluated for their antimigratory activity and cytotoxicity. This was accomplished by scoring wounds as opened or closed as a function of time following wounding to determine the time to closure. Cell viability was determined by the trypan blue dye exclusion assay conducted at the end of each experiment, with the ratio of dye-non-excluding (dead) to dye-excluding (live) cells compared with the control, described in greater detail in Example 7.

Three compounds (90, 92, and 94) of the library were found to inhibit wound closure or were cytotoxic at 24 hours after wounding at 50 μm and 10 μm concentrations and were inactive at 2 μm. None of the other compounds in the library exhibited any effect on the rate of wound closure, the morphology of the cells or their viability compared to the control. Therefore, compounds 90, 92, and 94 were examined further in quantitative wound closure assays, over a more finely divided range of concentrations. Cell monolayers in 24-well tissue culture plates were treated with different concentrations of each compound 30 minutes before wounding and then wounded, as described above.

Digital images of the wounds were captured immediately after wounding and at 3 h, 6 h, 9 h, 12 h, and 24 hours post-wounding. The open wound areas, as a function of time after wounding, were determined with NIH Image J software to establish the mean percent wound closure over time for each treatment and parallel controls, as previously described. The mean percent wound closure values at 9 hours post-wounding for all concentrations up to the maximal subtoxic concentration were subjected to nonlinear regression to calculate $IC_{50}$ values and 95% confidence intervals for inhibition of wound closure.

Compounds 90, 92 and 94 inhibited cell migration over a range of concentrations below the threshold at which cell death first became apparent, suggesting that their antimigratory activity was separate from—and not just a secondary consequence of—general cytotoxic effects. Their $IC_{50}$ values for inhibition of cell migration were comparable with that of the natural product migrastatin, which has an $IC_{50}$ of 29 μm and has served as a lead for the subsequent development of more potent analogues.

EXAMPLE 6

Cell migration is a necessary condition for the metastasis of solid tumors. A major determinant of the metastatic potential of a cancer cell is its ability to invade through extracellular matrix barriers. Therefore, compounds 90, 92 and 94 were tested for their activities using a cell invasion assay. Of the three antimigratory compounds, compound 94 shown in FIG. 8 displayed the broadest range of subtoxic activity against cell invasion.

Compounds 90, 92, and 94 were analyzed for their ability to inhibit the invasion of cells through Matrigel in a cell invasion assay. The assay was performed in transwell chambers according to the manufacturer's instructions (BD Biosciences). The polycarbonate membranes (8 μm pore size) of the upper chambers were coated with Matrigel (25 μg). Growth medium containing the tested compound or DMSO alone was added to the lower chambers (600 mL per well in 24-well BD Falcon TC companion plates). MDA-MB-231 cells in serum-free DMEM containing the tested compound or DMSO alone were added to the upper chambers (100 mL chamber of a 5×10⁴ cells per mL suspension). In all cases, the final DMSO concentration was 0.05%. Cells were incubated at 37° C. under 5% $CO_2$ for 24 hours. After removing noninvaded cells from the upper surface of the membrane with a cotton swab, the invaded cells on the lower surface were fixed with MeOH, stained with crystal violet solution, rinsed with water, air-dried, and then counted by using an inverted microscope. In parallel experiments, cell viability, determined using the trypan blue dye exclusion assay at various concentrations of the tested compounds, was evaluated under the conditions of the cell invasion assay.

EXAMPLE 7

Compounds 90, 92 and 94 were also evaluated in a tetrazolium salt-based cell proliferation and viability assay. The compounds did not inhibit cell growth at concentrations at which they inhibited cell migration and invasion, but did become cytotoxic at higher concentrations over a very narrow range, with minimum lethal concentration (MLC) values similar to those in Table 1 determined from the trypan blue dye exclusion assay conducted at the end of the wound closure experiments.

The cell proliferation and cell viability assay was conducted according to the manufacturer's instructions (CCK-8; Dojindo Molecular Technologies). MDA-MB-231 cells were plated in 96-well tissue culture plates (125 mL per well of a 4×10⁴ cells per mL suspension in growth medium) and incubated for 24 hours at 37° C. under 5% $CO_2$. The cells were then treated with the tested compounds at various concentrations or with DMSO alone. In all cases, the final DMSO concentration was 0.05%. At the same time, other cells from parallel plates were analyzed using the CCK-8 assay to establish the cell density at the start of the experiment. After 48 hours of incubation, the cell numbers for the experimental samples were determined and compared with the initial cell numbers. A cytostatic effect was defined as a reduction in cell number relative to the 48 hour control that did not fall significantly below the mean initial cell number. A cytotoxic effect was defined as a reduction in cell number that was significantly below that of the mean initial cell number.

Some of the results of the wound closure, trypan blue dye exclusion and tetrazolium salt assays of compounds 90, 92 and 94 are tabulated in Table 1. The Minimum Inhibitory Concentration (MIC) column of Table 1 represents the lowest concentration tested at which there was statistically significant inhibitory activity in the wound closure assay as determined by unpaired, two-tailed Student's t-tests (P<0.05).

Half-maximal inhibitory concentration ($IC_{50}$) values shown in Table 1 were calculated for inhibition of wound closure at 9 hours post-wounding from concentration—response profiles for a range of subtoxic concentrations (n=7–9 wounds from three independent experiments). The 95% confidence interval (CI) of the $IC_{50}$ for the compounds is also shown as a column in Table 1.

Minimum lethal concentration (MLC) represents the lowest concentration tested at which there was statistically significant cell death, measured using the trypan blue dye exclusion assay, by the end of wound closure experiments. The minimum lethal concentration (MLC) for compound 94 under the conditions of the cell invasion assay was 50 μm. In the cell invasion assay, cells were at a lower density than in the wound closure assay, and compounds were added at the same time as the cells, rather than after attachment and growth.

Figure 8:
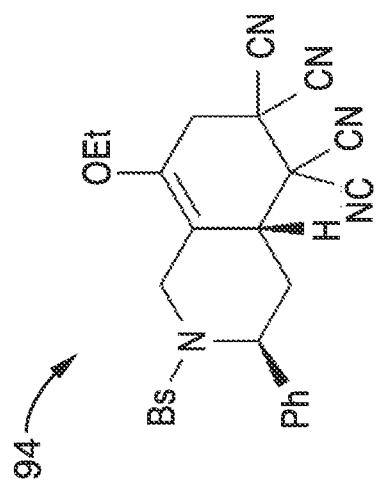
FIG. 8 is a diagram of a compound 94 that was shown to inhibit cell migration of MDA-MB-231 human breast cancer cells.
Figure 7:
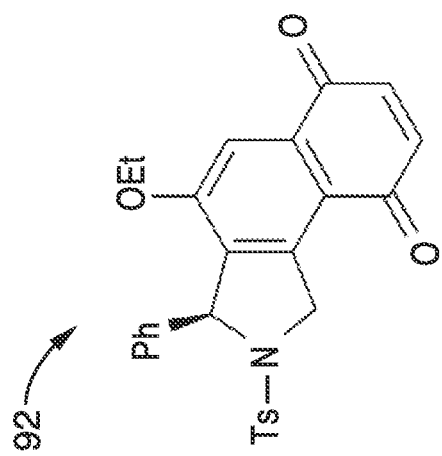
FIG. 7 is a diagram of a compound 92 that was shown to inhibit cell migration of MDA-MB-231 human breast cancer cells.
Figure 6:
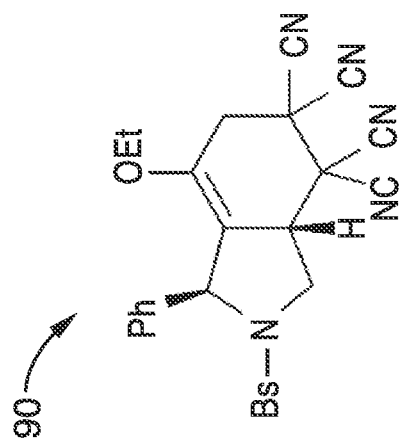
FIG. 6 is a diagram of a compound 90 that was shown to inhibit cell migration of MDA-MB-231 human breast cancer cells.

The structures of compounds 90, 92 and 94 are that were evaluated are included on Table 1 and FIG. 6, FIG. 7 and FIG. 8. As indicated previously, the groups labeled Bs=benzenesulfonyl and Ts=tosyl (p-toluenesulfonyl) in the compounds shown in these figures. The Et (ethyl) group of compounds 90, 92 and 94 can also be substituted with other alcohol groups such as 3, 4, and 5-carbon alkyl groups.

Therefore, the three compounds 90, 92 and 94 were shown to inhibit cell migration and invasion at subtoxic concentrations, but, interestingly, they do not exhibit subtoxic antiproliferative (cytostatic) activity that is separable from cytotoxicity. The findings suggest that these compounds have specificity for targets involved in modulating cell migration and invasion over proliferation. Compounds 90, 92 and 94 may therefore serve as leads for the development of targeted inhibitors of cell migration and invasion to block breast cancer metastasis.

From the discussion above it will be appreciated that the invention can be embodied in various ways, including the following:

1. A method for producing a structurally and stereochemically diverse library of compounds, comprising: (a) providing molecules with at least one $(\alpha,\beta)$-unsaturated ester; (b) methylenating the $(\alpha,\beta)$-unsaturated esters to produce a variety of ethoxy dienes; and (c) performing a Diels-Alder reaction between the ethoxy dienes and an electron-deficient dienophile to produce a library of compounds.

2. The method of any preceding embodiment, further comprising: identifying Diels-Alder reaction products that contain enol ether units; and hydrolyzing the enol ether units to form ketones.

3. The method of any preceding embodiment, wherein the molecules with at least one $(\alpha,\beta)$-unsaturated ester comprise compounds formed through phosphine-catalyzed ring formation between allenoates and imines.

4. The method of any preceding embodiment, wherein the imines are secondary aldimines with substituents selected from the group of substituents consisting of benzenesulfonyl, tosyl (p-toluenesulfonyl), phenyl, 4-MeC$_6$H$_4$, 4-EtC$_6$H$_4$, 4-ClC$_6$H$_4$, 3-ClC$_6$H$_4$ 2-thiophenyl and 1-naphthyl.

5. The method of any preceding embodiment, wherein the dienophile is a secondary aldimine of the formula comprising: Ar—C=N—P, wherein Ar is a substituent selected from the group of substituents consisting of phenyl, 2-thiophenyl, 4-EtC$_6$H$_4$ and 4-ClC$_6$H$_4$; and P is a substituent selected from the group of substituents consisting of benzenesulfonyl and p-toluenesulfonyl.

6. The method of any preceding embodiment 1, wherein the dienophile is selected from the group of dienophiles consisting of N-phenylmaleimide, N-ethylmaleimide, N-benzylmaleimide, N-phenyltriazolinedione, tetracyanoethylene, benzoquinone, and 2,6-dichlorobenzoquinone.

7. The method of any preceding embodiment, further comprising: surveying the biological or chemical activity of each compound in the library; and identifying the steriochemical structure of biologically or chemically active compounds.

8. A method for generating a library of heterocyclic compounds, comprising: (a) forming pyrrolines and tetrahydropyridines with at least one $(\alpha,\beta)$-unsaturated ester through phosphine-catalyzed ring formation between allenoates and imines; (b) methylenating the unsaturated esters with Tebbe reagent to produce a variety of ethoxy dienes; and (c) performing a Diels-Alder reaction between the Tebbe reaction products and electron-deficient dienophiles to produce a library of compounds.

9. The method of any preceding embodiment, wherein the imines are secondary aldimines with substituents selected from the group of substituents consisting of benzenesulfonyl, tosyl (p-toluenesulfonyl), phenyl, 4-MeC$_6$H$_4$, 4-EtC$_6$H$_4$, 4-ClC$_6$H$_4$, 3-ClC$_6$H$_4$ 2-thiophenyl and 1-naphthyl.

10. The method of any preceding embodiment, wherein the dienophile is a secondary aldimine of the formula comprising: Ar—C=N—P, wherein Ar is a substituent selected from the group of substituents consisting of phenyl, 2-thiophenyl, 4-EtC$_6$H$_4$ and 4-ClC$_6$H$_4$; and P is a substituent selected from the group of substituents consisting of benzenesulfonyl and p-toluenesulfonyl.

11. The method of any preceding embodiment, wherein the dienophile is selected from the group of dienophiles consisting of N-phenylmaleimide, N-ethylmaleimide, N-benzylmaleimide, N-phenyltriazolinedione, tetracyanoethylene, benzoquinone, and 2,6-dichlorobenzoquinone.

12. The method of any preceding embodiment, further comprising: surveying the biological or chemical activity of each compound in the library; and identifying the steriochemical structure of biologically or chemically active compounds.

13. A method for inhibiting human breast cancer cell migration, comprising: (a) synthesizing an antimigratory agent, said synthesis comprising: (i) forming a pyrroline with an $(\alpha,\beta)$-unsaturated ester through phosphine-catalyzed ring formation between ethyl allenoate and a secondary aldimine; (ii) methylenating the $(\alpha,\beta)$-unsaturated ester with Tebbe reagent to produce an ethoxy diene; and (iii) performing a Diels-Alder reaction between the Tebbe reaction products and a tetracyanoethylene or a benzoquinone dienophile to produce a compound; and (b) administering a therapeutic amount of the compound to human breast cancer cells.

14. The method of any preceding embodiment, wherein the therapeutic amount of compound comprises a 50 micromolar to 150 micromolar solution.

15. A method for inhibiting human breast cancer cell migration, comprising: (a) synthesizing an antimigratory agent, said synthesis comprising: (i) forming a tetrahydropyridine with an $(\alpha,\beta)$-unsaturated ester through phosphine-catalyzed ring formation between ethyl allenoate and a secondary aldimine; (ii) methylenating the $(\alpha,\beta)$-unsaturated ester with Tebbe reagent to produce an ethoxy diene; and (iii) performing a Diels-Alder reaction between the Tebbe reaction products and a tetracyanoethylene dienophile to produce a final compound; and (b) administering a therapeutic amount of the compound to human breast cancer cells.

16. The method of any preceding embodiment, wherein the therapeutic amount of compound comprises a 50 micromolar to 150 micromolar solution.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Inhibition of Migration of MDA-MB-231 Human Breast Cancer Cells

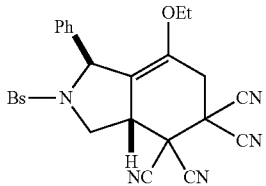

90

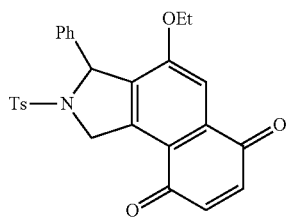 [SMILES: CCOc1cc2c(c3c1C(c1ccccc1)N(S(=O)(=O)c1ccc(C)cc1)C3)C(=O)C=CC2=O]

92

TABLE 1-continued

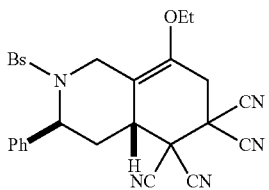

94

| Compound | MIC [µm] | IC$_{50}$ [µm] | 95% CI [µm] | MLC [µm] |
|---|---|---|---|---|
| 90 | 5 | 43.1 | 39.9-46.6 | 150 |
| 92 | 5 | 14.8 | 13.1-16.7 | 50 |
| 94 | 5 | 21.6 | 19.1-24.5 | 100 |

What is claimed is:

1. An antimigratory compound having the formula comprising:

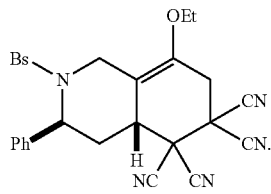

* * * * *